United States Patent [19]

Wang et al.

[11] 4,382,800
[45] May 10, 1983

[54] FREE AMINE-CONTAINING POLYMERIC DYES

[75] Inventors: Patricia C. Wang; Robert E. Wingard, Jr., both of Palo Alto, Calif.

[73] Assignee: Dynapol, Palo Alto, Calif.

[21] Appl. No.: 306,368

[22] Filed: Sep. 28, 1981

Related U.S. Application Data

[63] Continuation of Ser. No. 832,254, Sep. 12, 1977, abandoned, which is a continuation of Ser. No. 638,730, Dec. 8, 1975, Pat. No. 4,051,138.

[51] Int. Cl.$^3$ .................. D06P 3/04; C09B 69/10
[52] U.S. Cl. .................................. 8/404; 8/647; 8/917; 525/253; 525/375; 525/328.2; 546/68; 564/66; 564/68; 564/308; 526/307.1
[58] Field of Search .................................. 8/647, 404

[56] References Cited

U.S. PATENT DOCUMENTS

| | | |
|---|---|---|
| 3,304,297 | 2/1967 | Wesmann et al. ............ 8/528 |
| 3,337,288 | 8/1967 | Horisuchi et al. ............ 8/552 |
| 3,567,678 | 3/1971 | Kalopissis ............ 528/345 |
| 3,920,855 | 11/1975 | Dawson et al. ............ 426/250 |
| 4,051,138 | 9/1977 | Wans et al. ............ 8/647 |
| 4,182,885 | 1/1980 | Bunes ............ 526/259 |
| 4,206,240 | 6/1980 | Bunes ............ 525/282 |

*Primary Examiner*—A. Lionel Clingman
*Attorney, Agent, or Firm*—Burns, Doane, Swecker & Mathis

[57] ABSTRACT

Soluble polymeric colorants composed of free amine groups and chromophoric groups covalently bonded to an organic backbone are disclosed. The number of free amine groups is not less than one-half the number of chromophoric groups. The colorants are characterized by being free of sulfonate, phosphonate and carboxylate groups. The preparation and use of these colorants is also disclosed.

1 Claim, No Drawings

FREE AMINE-CONTAINING POLYMERIC DYES

REFERENCE TO RELATED APPLICATION

This is a continuation of Application Ser. No. 832,254, filed Sept. 12, 1977, and now abandoned which is a continuation-in-part of copending U.S. patent application, Ser. No. 638,730, filed Dec. 8, 1975, now U.S. Pat. No. 4,051,138.

BACKGROUND OF THE INVENTION

1. Field of the Invention

This invention relates to polymeric coloring compositions. More particularly, it relates to soluble polymeric colorants, characterized as containing a substantial proportion of free amine groups.

2. Background Art

Polymeric colorants are composed of optically chromophoric groups bound to or into polymers. Such materials may be found in the prior art, for example, in Horiguchi et al.'s U.S. Pat. No. 3,337,288, granted on Aug. 22, 1967; in Wegman et al.'s U.S. Pat. No. 3,304,297, granted on Feb. 14, 1967; in Japanese Published Patent Application 14,434, published in 1966 and cited at 66 Chemical Abstracts 19843 j; in the article by Ida et al. appearing at pages 524-30 of volume 89(4) of YAKUGAKU ZASSHI; in Kalopissis's U.S. Pat. No. 3,567,678, granted on Mar. 2, 1971; in Dawson et al.'s U.S. Pat. No. 3,920,855, issued on Nov. 18, 1975; in the article by Dawson et al. appearing at pages 5996-6000 of volume 98:19 of JACS, and in Otteson et al.'s South African Patent Number 76/7083, filed Dec. 7, 1976. These and other references make it clear that in certain applications polymeric dyes can offer real, functional advantages. Their larger molecular size reduces their diffusivity and increases their film-forming properties. In food coloring applications polymeric colors can offer yet another advantage which is pointed out in the already-noted Ida et al., Dawson et al., and Otteson et al. references. If a polymeric color molecule has a large enough molecular weight and size, it will be too large to be absorbed from the gastrointestinal tract when eaten with food. This means that the color will not pass into the body, and any risk of systemic toxicity is essentially eliminated.

The polymeric colorant products disclosed in the cited Otteson and Dawson references and also, in fact, the products claimed in this application's parent may be classified as colorants that are water-soluble as a result of the presence of anionic groups such as sulfonates, sulfamates, phosphonates and the like, imparting hydrophilicity to the polymers. Such a method of solubilizing offers the major advantage of imparting water-solubility in a wide range of aqueous environments.

The present invention concerns soluble polymeric colorants which have amine solubilizing groups, but no significant number of anionic solubilizing groups. These materials offer particular advantages. They tend to be soluble in water at pHs of from about 2.0-4.0, but are insoluble in water otherwise. Their amine groups can ionically bond to negatively charged substrates. When applied to such a substrate, they are relatively colorfast not only because of their being bonded to the substrate, but also because of their limited solubility.

STATEMENT OF THE INVENTION

A new and advantageous form of soluble polymeric coloring composition has now been found. These colorants contain a plurality (m) of optically chromophoric groups covalently linked to carbon atoms of a hydrocarbon polymer backbone. Also covalently attached to this backbone, but to different carbon atoms thereof, are a plurality (n) of independent free amine groups selected from among the primary and secondary lower alkyl-amine groups. n and m are selected such that there is not less than one free alkylamine group for each two optically chromophoric groups, and the colorant molecule has a molecular weight of not less than 2,000 daltons.

Colorants of this invention have the advantages of being soluble in pH 2.0–4 aqueous media, but otherwise being relatively insoluble in water and of being capable of ionically bonding to substrates such as proteinaceous fibers and the like, and thus bonding relatively quite fast to such substrates. These colorants are soluble in polar aprotic solvents and in wet water-miscible solvents such as alcohols. Because of their polymeric nature, they are of a molecular size which precludes their absorption (passage) through the walls of the gastrointestinal tract or through other body surfaces so that they present minimal risks of systemic toxicity when consumed or used on the surface of the body.

DETAILED DESCRIPTION OF THE INVENTION

The polymeric colorants of this invention consist of organic polymeric molecules. These molecules have hydrocarbon polymer chain backbones. Free amine groups and separate optical chromophoric groups are chemically (covalently) attached to carbon atoms of the polymeric backbone.

The Free Amine Groups

The free amine groups employed in the present colorants are defined to be primary or secondary lower alkyl amine groups. Primary amine groups are preferred free amine groups. These groups are represented structurally as

groups wherein $R_4$ is hydrogen or a 1 to 4 carbon saturated alkyl such as methyl, ethyl, propyl, isopropyl or butyl, or a continuation thereof. Preferably, $R_4$ is hydrogen or methyl, and more preferably $R_4$ is hydrogen. These free amine groups may be attached directly to carbon atoms of the backbone, or they may be attached through an olefinically saturated lower hydrocarbon group (especially alkyl) which is itself pendant from the backbone. This configuration is shown as

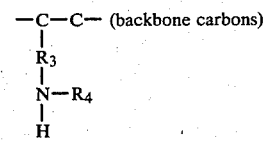

wherein $R_4$ is as previously defined and $R_3$ is selected from a carbon-nitrogen single bond, a 1 to 4 carbon saturated alkylene bridge, such as methylene, ethylene, propylene or butylene or a six carbon aromatic bridge—i.e., phenylene.

The Chromophoric Groups and Their Attachment

Also attached to the backbone are a plurality of optically chromophoric groups. These groups, denominated "Chrom" in the structural formulae, are organic groups which present a visible color to the human eye. Suitable chromophores should contain no significant number of anionic groups such as sulfonates, sulfamates, or phosphonates. These groups are covalently bonded to the backbone in one of two configurations. First, they may be covalently bonded directly to backbone carbon atoms in a

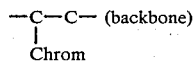

configuration. Second, and this is a preferred arrangement, they may be linked through amine groups in an

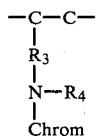

configuration, wherein $R_3$ and $R_4$ are as previously defined.

The Backbones

The backbones employed in the present colorants are hydrocarbons. They are olefinically saturated, that is they do not contain intentionally incorporated olefinic unsaturation. Preferably, they are essentially linear, containing no appreciable long chain branching. The length of the backbone should be such as to assure a molecular weight of at least 2000 Daltons to the final colorant molecule.

The Structure of The Colorants

The present colorants may be shown by following structural formula I.

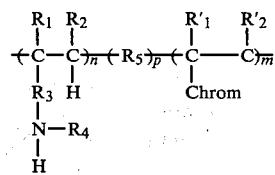

wherein $R_1$ and $R_1'$ independently are hydrogen or a lower saturated alkyl of up to 4 carbon atoms, i.e., methyl, ethyl, propyl or butyl; $R_2$ and $R_2'$ independently are hydrogen, a lower saturated alkyl of up to 4 carbon atoms or an aromatic hydrocarbon of about 6 carbon atoms, i.e., phenyl; $R_3$ is most commonly a simple carbon to nitrogen single covalent bond, but also may be a 1 to 4 carbon atom lower saturated alkylene bridge, or a 6 carbon atom aromatic (phenylene) bridge; $R_4$ is hydrogen or a lower saturated alkyl of 1 to 4 carbon atoms; $R_5$ is a carbon to carbon single bond, ethylene, a 1 to 4 carbon saturated alkyl-substituted ethylene, a 6–8 carbon aromatic-substituted ethylene, or an oxyhydrocarbon or nitrohydrocarbon as hereinafter shown. Chrom is an optically chromophoric group and n, p, and m are numbers such that n is at least ½ m and the sum of n+m+p is such as to assure a molecular weight of at least 2000 to the colorant molecule.

In the preferred embodiment wherein the chromophore units are attached via amine sites, the colorants have the "amine-site" structure shown in Formula II.

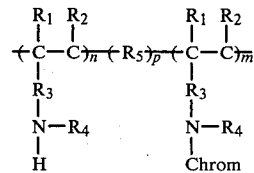

wherein $R_1$, $R_2$, $R_3$, $R_4$, $R_5$, Chrom and n, m and p are as previously defined. Very preferably $R_1$ and $R_2$ are independently selected from hydrogen, ethyl or methyl, $R_3$ is a carbon to nitrogen single bond, methylene or ethylene, $R_4$ is hydrogen, methyl or ethyl, $R_5$ is a carbon to carbon single bond, ethylene, a 1 to 4 carbon saturated alkyl substituted ethylene, and Chrom, n, m and p are as previously defined. Most preferably, $R_1$, $R_2$, and $R_4$ are hydrogen and $R_3$ is a carbon to nitrogen single bond and $R_5$ is a carbon to carbon single bond.

The polymeric colorants may be formed by several methods. For one, an ethylenically unsaturated chromophore or precursor may be copolymerized with the free amine group containing monomer. More preferably, however, a chromophore is reacted with and bonded to a reactive site on a performed amine site containing backbone. In the preferred embodiment, this reactive site is a portion of the total amine sites originally incorporated into the backbone. The amine groups used as active sites may be incorporated into the chromophore, that is, they may participate in the color imparting structure of the chromophore or they may be independent of the chromophore, serving only as a "color inert" point of attachment. This "amine-site linked" embodiment is preferred because of the simplicity of production which it enables. A homopolymeric or copolymeric backbone containing n+m amine groups is formed. Then, a portion (m) of these groups is used as chromophore attachment positions.

The following is a list of exemplary homopolymeric amine site-containing backbones preferred for use in the colorants of this invention: poly(vinylamine),

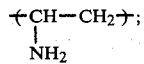

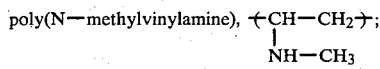

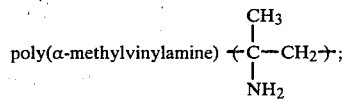

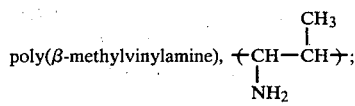

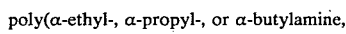

-continued

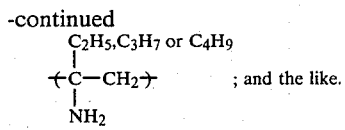
; and the like.

Preferred homopolymers include poly(vinylamine), poly(N-methylvinylamine), and poly(α-methylvinylamine).

The backbones may comprise added copolymeric units as well. These units, shown by $R_5$ in Formula I, need not be solely hydrocarbons but should only add hydrocarbon to the structural chain of the backbone and should not add anionic groups such as phosphonates, sulfonates or sulfamates. The added units include, for example, the hydrocarbons

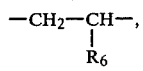

wherein $R_6$ is hydrogen, a 1 to 4 carbon alkyl or an aryl, alkaryl or aralkyl of from 6 to 8 carbons; the oxyhydrocarbons

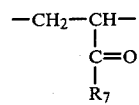

and

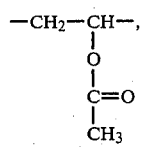

wherein $R_7$ is hydrogen, a 1 to 4 carbon alkyl, or a —O—$CH_3$ group; or a nitrilohydrocarbon

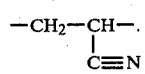

As is illustrated by these formulae, the sole contribution made to the backbone chain by these materials is hydrocarbon.

Size Of The Colorants

The length (or size) of the backbone chain and hence values of n, m and p are of importance. Clearly, since at least one chromophoric group is attached to the backbone through amine linkages and at least one additional cationic amine is present, the backbone must contain at least two such amines. If one is to obtain most advantageous polymer properties with the polymeric colors of this invention, n+m, that is the number of amino groups on a polymer chain, should be at least 20. However, if n+m is substantially greater than about 3000, say 5000 or 10,000, generally the performance as colorants of the final polymers decreases. Thus, a preferred size of backbone obtained when n+m is between 20 and 3000, more preferably when n is between 40 and 2000 and most preferably when n is between 100 and 1500.

Formulae I and II show n free amine groups and m chromophore groups in their structures. n and m are related numbers. 2n is greater than m. Preferably, n is greater than 1 times m, but not greater than about 6 times m. The upper limit on n is dictated by practical considerations. If n is greater than 6m, the coloring power of the polymeric colorant is generally low since the colorant does not carry a sufficient number of chromophores. More preferably, n is from 1.2 to 4 times m with a most preferred relationship being n equal to from 1.3 to 3.5 times m.

Formulae I and II also show p $R_5$ copolymerizate units. These copolymerizate units are optional so p may equal 0. p may also be as large as about 2(n+m); preferably p is 0 or up to about 1(n+m); most preferably p is 0.

The backbones are generally prepared separately prior to chromophore attachment. This may be done by free radically polymerizing olefinically unsaturated amine- or amine-precursor-substituted monomers. A number of representative backbone preparations are depicted herein in Examples I–VI. Alternative preparations are set forth at Kurtz and Disselnkotter, U.S. Pat. No. 3,424,791; Hanford and Stevenson, U.S. Pat. No. 2,276,840; Hanford and Stevenson, U.S. Pat. No. 2,231,905; Horwitz and Aschkenasy, Belgian 637,380; Hart, *Makromol. Chem.*, 32, 51(1959); Hart, *J. Polymer Science*, 29, 629 (1958); Blomquist, et al., *J. Am. Chem. Soc.*, 67, 1519 (1965); Kurtz and Disselnkotter, *Liebigs Ann. Chem.*, 764, 69 (1972); Bailey and Bird, *J. Org. Chem.*, 23, 996 (1958); and Seki et al., *Chem. Pharm. Bull.*, 20, 361 (1972); which disclosures are expressly incorporated by reference into this patent application.

A very preferred embodiment of this invention comprises poly(vinylamine) homopolymer of molecular weight of 40,000 to 130,000 Daltons (i.e., containing from about 1000 to 3000 amine groups) having from 20 to 67% of its amine groups substituted with chromophore units.

When experimental molecular weights are noted herein they have been derived by gel permeation techniques. In the primary technique, a silanized porous glass support is used with 0.01 M LiBr in DMF eluent. Detection is by refractometer with standardization being based on purchased polystyrene standards. Expressed in terms of molecular weight, examples of backbones meeting the general size criteria (n=20 to 3000) include poly(vinylamine) of molecular weight 860 to 129,000; poly(α, β or N-methylvinylamine) of molecular weight 1180 to 177,000 and poly(α or β-butylvinylamine) of molecular weight 2020 to 303,000. In the same terms, backbones meeting the most preferred size criteria (n=100 to 1500) include poly(vinylamine) of molecular weight 4300 to 64,500 and poly(α-methylvinylamine) of molecular weight 5900 to 88,500. Further preferences in molecular size will be noted when the colorant products are to be used as colorants for edible compositions. These will be set forth hereinafter.

More Detailed Description of Chromophores

The chromophoric groups employed in the present coloring compositions are organic optical chromophores. These materials are defined to be organic chemical groups which exhibit a visual color to the human eye when attached to a polymeric backbone. These chromophores can be selected from a wide range of classes of groups, including the azo chromophores, anthraquinone chromophores, xanthene chromophores, triphenylmethane chromophores, indigoid chromophores and the like. These classes of chromophores are merely representative—other similar materials also being usable. Among these chromophores, special preference is given to anthraquinone chromophores because of their great stability under stressful conditions of heat and light and the wide range of colors which they permit. Among chromophores, those which contain no anionic groups such as sulfonates, sulfamates or phosphonates, and are themselves water-insoluble, generally achieve most improved usefulness when used in the present polymeric form. A chromophore is defined as being water-insoluble if its solubility in room temperature water at neutral conditions (pH 7) is less than 500 parts per million weight (basis water).

Preferred anthraquinone chromophores in their unattached (monomeric) state have a leaving group such as a —Cl, —Br, —I, —SO$_3$Na, —N$_2^\oplus$Cl$^\ominus$, or —NO$_2$ group attached to their aromatic ring. This permits the chromophore's facile use in the preferred colorants wherein some backbone amines are used to couple chromophores. In this technique copper is used to catalyze the leaving groups' displacement by amines. In many case, no catalyst is required to effect the desired displacement. Several classes of anthraquinone chromophores deserve special mention:

Aminoanthraquinone chromophores of the structure of Formula III,

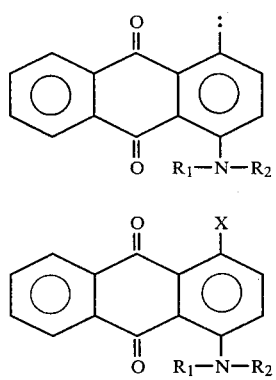

formed by coupling the monomer IIIA wherein R$_1$ is a hydrogen or a lower saturated alkyl of up to four carbon atoms, R$_2$ is hydrogen, a lower saturated alkyl of up to four carbon atoms or an aryl or alkaryl of from six to eight carbons and X is a leaving group. These are useful to give the range of blue colorants listed in Table I.

TABLE I

| COMPOUND | | |
|---|---|---|
| R$_1$ | R$_2$ | COLOR |
| hydrogen | hydrogen | purplish blue |
| hydrogen | methyl | greenish blue |
| hydrogen | ethyl, propyl or butyl | greenish blue |
| hydrogen | aryl | navy blue |

Anthrapyridones of the structure of Formula IV.

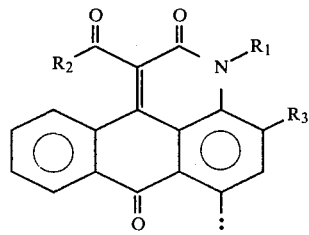

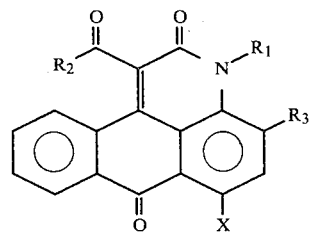

formed by coupling the corresponding monomer, wherein X is a leaving group, R$_1$ is a hydrogen, a lower saturated alkyl of 1 to 4 carbon atoms inclusive, an alkaryl or an aryl grouping of from 6 to 8 carbons, R$_2$ is 1 to 4 carbon saturated alkyl, a 1 to 4 carbon saturated alkoxy, and R$_3$ is a hydrogen or a 1-4 carbon lower saturated alkyl. These chromophores are rich reds and violet-reds. Preferred among the anthrapyridones are these according to Formula IV wherein R$_1$, R$_2$, and R$_3$ are shown in Table II.

TABLE II

| R$_1$ | R$_2$ | R$_3$ |
|---|---|---|
| hydrogen | 2-5 carbon alkyl | 1-4 carbon alkyl |
| hydrogen | methyl | methyl |
| hydrogen | methoxy | 1-4 carbon alkyl |
| hydrogen | methoxy | methyl |
| hydrogen | ethoxy | 1-4 carbon alkyl |
| hydrogen | ethoxy | methyl |
| methyl | methyl | hydrogen |
| methyl | phenyl | hydrogen |
| methyl | ethoxy | hydrogen |

Anthrapyridines of the structure of Formula V:

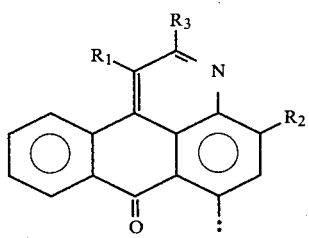

which are formed by coupling the corresponding monomeric chromophore

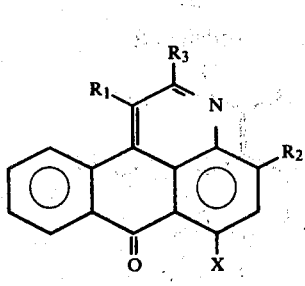

wherein X is a leaving group, $R_1$ is a 2 to 5 carbon lower saturated carbalkoxy, a 2 to 5 carbon lower saturated alkyl, an aroyl, an aryl or substituted (halo, nitro, alkoxy, or alkyl) aryl grouping of about 6 to 9 carbons, $R_2$ is hydrogen or a 1 to 4 carbon lower alkyl, and $R_3$ is a 1 to 3 carbon lower saturated alkyl, a 1 to 3 carbon lower saturated alkoxy, an alkaryloxy (i.e., benzyloxy) of about 7 to 9 carbons, or an aryl grouping of about 6 carbons. These colorants range in hues from yellows to reds to brown. Preferred among the anthrapyridines are those according to Formula V where $R_1$, $R_2$, and $R_3$ are shown in Table III.

TABLE III

| $R_1$ | $R_2$ | $R_3$ |
|---|---|---|
| carbethoxy | methyl | methyl |
| carbomethoxy | methyl | methyl |
| carbethoxy | methyl | methoxy |
| carbethoxy | methyl | ethoxy |
| carbethoxy | methyl | benzyloxy |
| phenyl | methyl | methoxy |
| phenyl | methyl | ethoxy |
| phenyl | methyl | benzyloxy |

Pyridinoanthrone dyes of the structure of Formula VI:

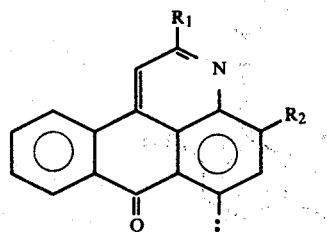

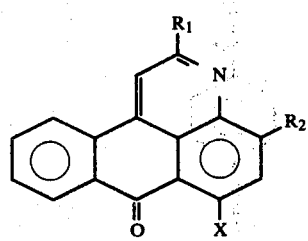

may also be used. These are formed by coupling the corresponding monomeric chromophore wherein $R_1$ is hydrogen or a 1 to 4 carbon saturated alkyl and $R_2$ is a hydrogen or a 1 to 4 carbon alkyl.

Anthrapyrimidines of the structure of Formula VII:

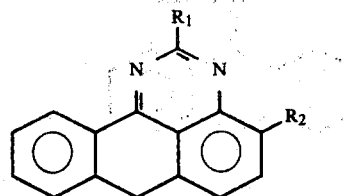

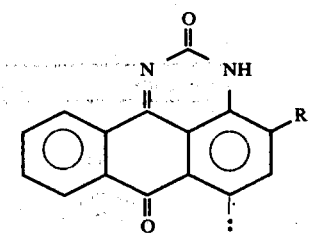

formed by coupling the monomeric chromophores of the formula wherein $R_1$ is hydrogen, a 6 carbon aryl, a 1 to 4 carbon saturated alkyl or a halogen as described in U.S. Pat. No. 1,947,855 which deals with monomeric colorants. $R_2$ is a hydrogen or 1 to 4 carbon alkyl. These materials are reds and yellows.

Anthrapyrimidones of the structure of Formula VIII:

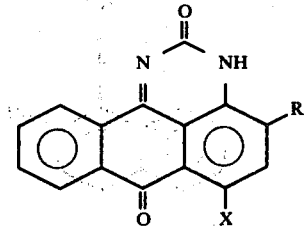

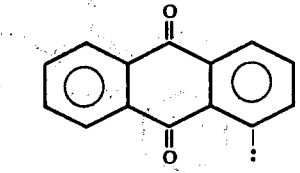

formed by coupling the monomeric chromophores. These materials are violets. R is a hydrogen or 1 to 4 carbon alkyl. Substitution of 4 position by amino group gives violet dye (U.S. Pat. No. 1,004,107).

The anthraquinones of the structure of Formula IX:

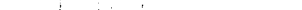

formed by coupling the monomeric chromophores shown in Formula IX A. These materials are reds.

Anthrapyridones of the structure of Formula X:

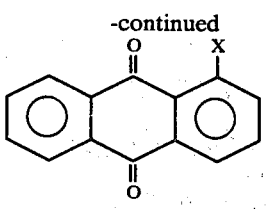

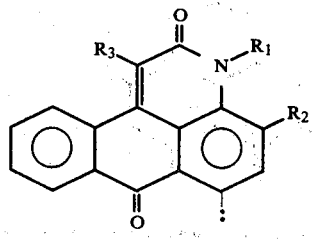

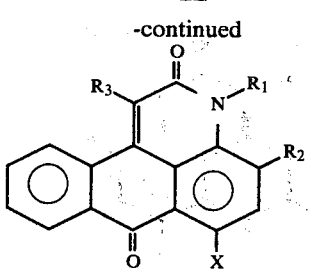

formed by coupling the monomeric chromophores of X A, wherein $R_1$ is hydrogen, methyl, or aryl, $R_2$ is hydrogen or 1 to 4 carbon lower alkyl and $R_3$ is hydrogen, a halogen (i.e., Br or Cl), cyano (i.e., —CN), $NO_2$ or a lower alkyl of 1 to 4 carbon atoms.

Among the azo colorants, those having monomeric forms with a sulfonyl chloride comprise one preferred group since they may be easily attached to the amine backbone via the well known Schotten-Baumann reaction. Exemplary chromophores of this class and chlorosulfonyl precursors include the first four materials shown in Table IV. Also listed in Table IV are several nonazo chromophores which are attached via the Schotten-Baumann reaction.

TABLE IV

| Chromophore | Precursor |
|---|---|

TABLE IV-continued
| Chromophore | Precursor |
|---|---|
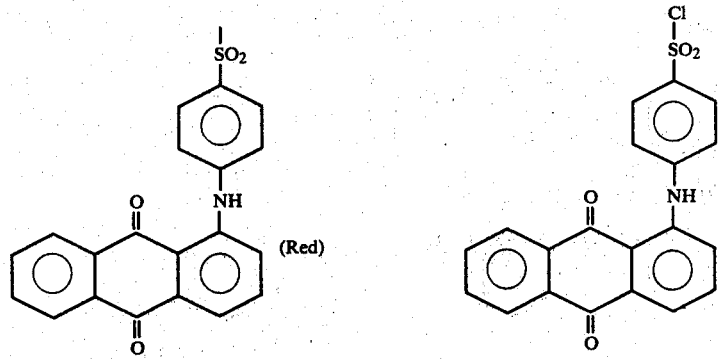
$R_1$ = H, or 1 to 4 C alkyl
$R_2$ = H, or 1 to 4 C alkyl
$R_3$ = 1 to 4 C alkyl or alkoxy
$R_4$ = H, or 1 to 4 C alkyl or alkoxy

TABLE IV-continued
| Chromophore | Precursor |
|---|---|
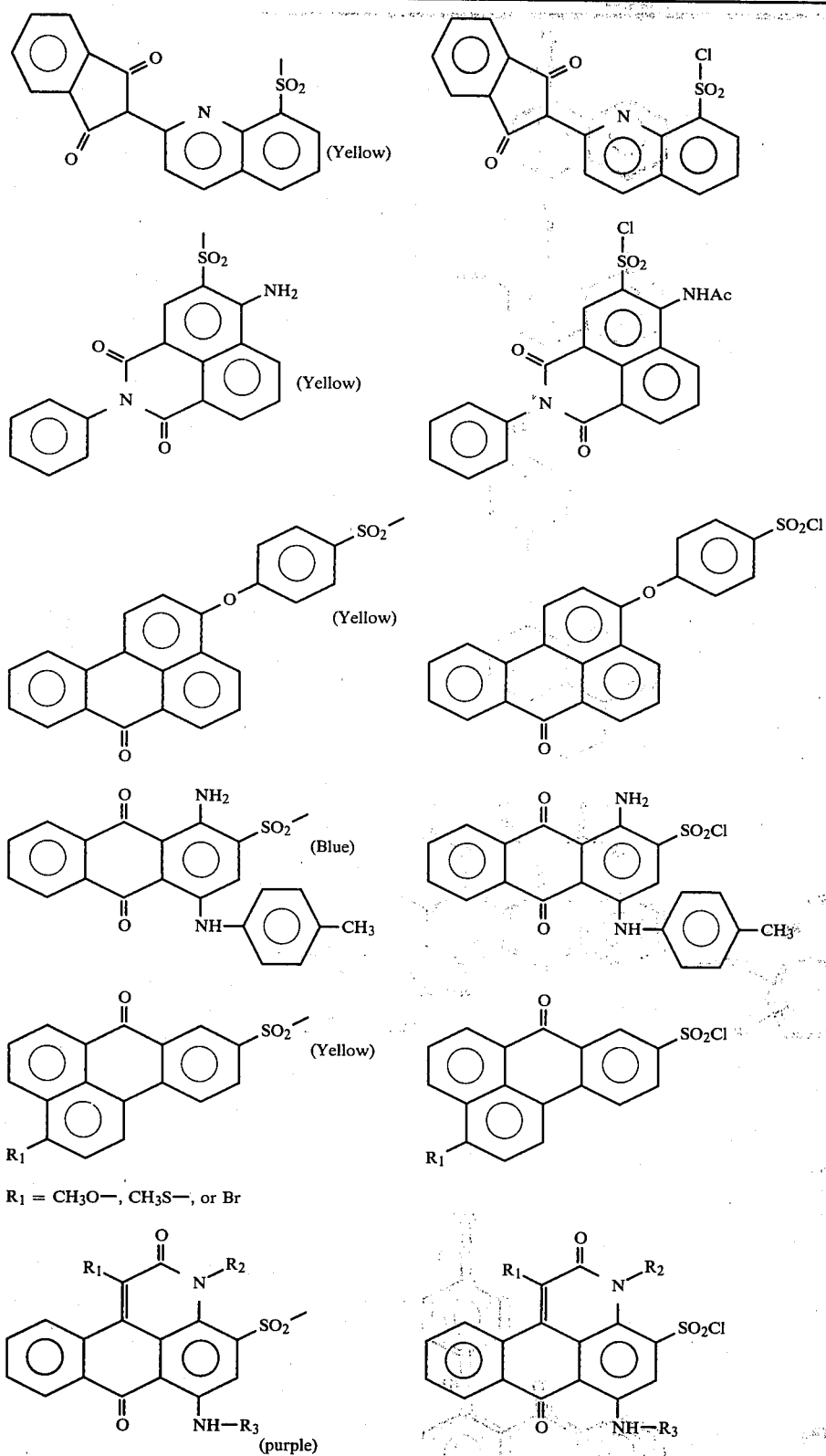
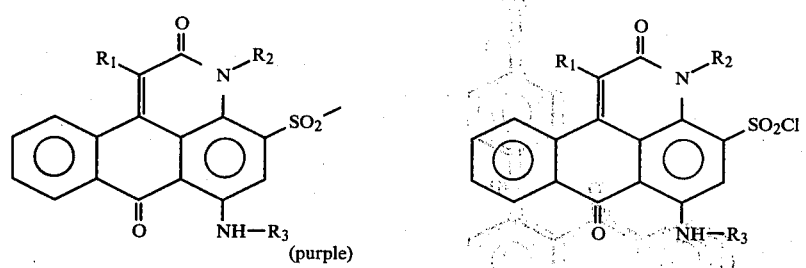

TABLE IV-continued

| Chromophore | Precursor |
|---|---|

R₃ = —CH₃ or —⟨phenyl⟩—CH₃

[Anthraquinone chromophore structure with R₁, N-phenyl-SO₂—, NH—R₂ substituents]  [Anthraquinone precursor structure with R₁, N-phenyl-SO₂Cl, NH—R₂ substituents]

Red as shown in Brit. Patent 525,091 (1941)

R₁ and R₂ = —CH₃ or —⟨phenyl⟩—CH₃

Preparation Of The Compounds

Conceptually, the compounds of this invention can be prepared by the following basic routes:

1. A polymerizable unsaturated amine or amine precursor can be copolymerized with a polymerizable unsaturated chromophore generally under free radical conditions. As a species of this process, an unsaturated amine or amine precursor can be copolymerized with an unsaturated amine-containing chromophore.

2. A polymerizable unsaturated amine or amine precursor can be copolymerized with a polymerizable unsaturated chromophore precursor also generally under free radical conditions to yield a polymer product which can be further processed to yield the desired amine containing-polymeric colorant.

3. A preformed backbone can be treated to attach amines and then to attach chromophores.

4. A preformed amine-containing backbone can be treated to attach chromophores to a portion of the amine groups.

Of these routes, the last is the most preferred. The first two routes suffer the disadvantage of not permitting the close control of molecular size which is achieved when a separate purified backbone is used. The third route conceptually may be used, but it generally is easier to incorporate amines directly when the backbone is being formed (as in route 4) rather than adding them to the backbone.

When this last route is followed, this first step involves obtaining an amine group-containing polymer backbone. In the case where poly(vinylamine) is the backbone, a full disclosure of one route to the polymer is given in U.S. Pat. No. 4,018,826, issued Apr. 19, 1977, by Gless et al., which application is herein incorporated by reference, and which route is exemplified herein as Example 1. In the case where the backbone is a poly(N-alkyl-vinylamine) such a material can be prepared by first reacting the corresponding N-alkylaminoethanol with an excess (preferably from 2 to 3 equivalents) of an acid anhydride, preferably acetic anhydride, at an elevated temperature, especially 75°–140° C., to yield in 5–60 minutes the bis-acetylated product which in the case where acetic anhydride is used has the formula

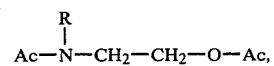

R is lower N-alkyl such as methyl and "Ac" are acetyl groups resulting from added acetic anhydride. The bis-acetylated product is pyrolyzed in vapor phase at 350°–600° C. to yield N-alkylvinylacetamide. The N-alkylvinylacetamide may be purified, by distillation or crystallization, and then polymerized in liquid phase in the presence of a suitable free radical initiator such as benzoyl hydroperoxide, other organic peroxides or other initiators such as AIBN or the like. This polymerization is generally carried out at a temperature of from 40°–100° C. and at a catalyst level of from 0.5–10% mole. It is generally carried out in a suitable organic liquid solvent, especially a lower alkanol, such as methanol, ethanol, or isopropanol. The resulting poly(N-alkylvinylamide) is then hydrolyzed by contact with an excess of a mineral acid, such as sulfuric, hydrochloric, perchloric or the like. This reaction is slow, requiring temperatures of at least 80° C. and as high as 175° C. and times of from 20–100 hours to go to completion. The hydrolysis product is the desired poly(N-alkylvinylamine) as the corresponding acid salt.

Once the backbone of choice is at hand, the next step in the preparation of the present compounds is to attach the chromophores. As pointed out in the description of suitable chromophores, there are several routes which find excellent application with certain classes of chromophores. For example, in the case of anthraquinone chromophores, it is possible to effect facile attachment by employing an anthraquinone bearing a leaving group attached to its aromatic ring. This leaving group is readily displaced by the backbone amine, generally in the presence of a copper catalyst, such as copper metal, cuprous oxide, copper I salts (cuprous chloride, etc.), copper II salts (cupric acetate, etc.) and complexes of copper and copper oxides or salts with a carbon carrier. One peculiarity of this reaction is the general need to employ a water-miscible cosolvent, such as methanol, ethanol, isopropanol, β-methoxy ethanol, diethylene glycol, ethylene glycol, N,N-dimethylformamide, dimethylsulfoxide, pyridine, tetrahydrofuran, N-methylpyrdlidone, with an about 5:1 to about 1:5 proportion of water.

This reaction is generally carried out at an elevated temperature, such as from about 80° C. to about 130° C., with the aqueous solvent reflux temperature often being most convenient.

When an azo chromophore is used, it is useful to employ a chromophore bearing a sulfonyl halide group or a methyl halide group, especially a methyl chloride or bromide group. These functionalities react with the amine backbone in the presence of base at pH 10-11 to form the desired couple. The former reaction is often referred to as the Schotten-Baumann reaction and goes smoothly at temperatures of from 0° to 60° C. and requires from about 2 to 12 hours to complete. In the case of azo compounds, it should be remembered that the polymer backbone with its amine groups could interfere with an attempt to diazotize an attached azo dye precursor. Thus, it is best when azo colors are involved to attach a diazotized (pre-coupled) color unit, rather than an undiazotized azo color precursor.

Use of Colorants

The colorants of this invention are soluble in water at pH 2.0-4.0, but relatively insoluble in water at other pHs. Solubility and insolubility may be quantified as follows: A material is insoluble if a saturated solution contains less than 500 ppm of the material. If the solution contains more, the material is soluble. This solubility at certain pHs offers advantages. The colorants may be applied in solution form to a substrate at pH 2.0-4.0. Then, the pH may be raised or lowered out of this soluble range. This causes the colorants to deposit on the substrate in a relatively permanent form. The colorants of this invention are positively charged. This means that they have special affinity for negatively charged substrates. This can have practical significance in the coloring of proteinaceous substrates such as wool or hair where the colorants achieve fast and relatively permanent coloration. In the coloring of hair or wool, a pH 2.0-4.0 solution of the colorant is applied and then the substrate is rinsed with neutral water. As the pH goes from 4.0 to 7, the colorant precipitates and is deposited on the substrate. Similarly, the colors can be applied to the substrate from an organic-water solution and rinsed with water to achieve fast and relatively permanent coloration. Suitable organic-water mixtures are water with from about 25% w to about 400% w (basis water) and preferably 50% to 300 by weight on the same basis of lower alkanol (of 1 to 4 carbons) such as methanol, ethanol, isopropanol or butanol, lower (2 to 3 carbon) alkandiols such as ethylene glycol or propylene glycol, and lower (3 to 5 carbon) alkanones such as acetone, methylethylketone or diethylketone.

The colorants also find use in other media such as in pigments, paints and the like. In another use, these colorants are admixed with edible materials, such as foods, beverages, medicines and the like. In this use it is most useful that the colorants be sized such that their molecular weight is not less than about 1500, preferably 2000 to 200,000, most preferably from 5,000 to 150,000. A colorant of this molecular weight has a molecular size which is too large to permit its absorption through the walls of the gastrointestinal tract and thus any risk of systemic toxicity arising from absorption of colorant from the gastrointestinal tract is eliminated. The colorants, because of their carbon-carbon backbone, and stable chromophore linkages, are essentially free of degradation at the conditions of passage through the gastrointestinal tract. This nonabsorbability feature may also be of advantage when coloring containers and wrappings for edibles, as any color which might migrate into the edible would be nonabsorbable.

In nonedible applications, such as in hair dyes, paints, dyes, etc., the colors of this invention may be used alone or may be admixed with other colorants in amounts of from about 20 ppm to 10% by weight basis colorant solutions.

In applications with edible materials, the colorants are added in an effective coloring amount, say from about 10 ppm to about 1% by weight (preferably from 10 ppm to 1000 ppm) to foods such as gelatin desserts, dispersed in cereals, added to fruits and other canned foods, to beverages such as carbonated beverages, for example orange, grape and cherry soda, wines and the like; and added to medicines such as cough elixers, cough drops and diverse other usually colored medicaments for man or beast alike. These applications involve the art known procedures of dispersing, dissolving or otherwise spreading the colorant upon or through the object to be colored.

The invention will be further described by references to the following examples. These are intended to provide an understanding of specific embodiments of the invention and are not to be construed as limiting the invention's scope.

EXAMPLE I

Preparation of poly(vinylamine) backbone:

A. Preparation of Vinylacetamide

To 9304 g of acetamide (technical) in a 12 liter reaction flask was added 62.2 ml of 6 M aqueous sulfuric acid followed immediately by 661 g of acetaldehyde (99+%). This mixture was stirred and heated until the internal temperature reached 78° C. (11 minutes) at which point the clear solution spontaneously crystallized, causing a temperature rise to 95° C. The reaction product, ethylidene-bis-acetamide, was not separated. Heating and stirring were continued for another 5 minutes to a temperature of 107° C. and a mixture of 150 g calcium carbonate (precipitated chalk) and 150 g of Celite ® diatomaceous earth powder was added. A first distillate fraction of water and acetamide was removed. The remaining material was transferred to a 22 liter flask and cracked at 35 mm Hg and 185° C. A fraction made up of vinylacetamide and acetamide, was taken overhead and pooled with seven other previously prepared batches. This pooled material was analyzed by NMR and found to contain 5.77 kg of vinylacetamide and 2.45 kg of acetamide.

B. Polymerization of Vinylacetamide

The vinylacetamide-acetamide mixture of Part A was mixed with 4.1 l of isopropanol and chilled overnight. Crystallized acetamide was removed by filtration. The filtrate plus rinses were diluted to a total isopropanol volume of 30.58 l. This solution was placed in a 50 l flask, deoxygenated and heated to 88° C. Then a solution of 233 g of AIBN polymerization catalyst in 830 ml of acetone was added and the mixture was stirred at temperature for about 4 hours to complete polymerization. The resulting thick solution was stripped of solvent to a volume of 15.3 liters and then poured into 95

1 of stirred acetone. The polymer formed a precipitate which was recovered by filtration, rinsed with acetone, and dried at 50° C. in a vacuum oven. The final product was 5 kg of poly(vinylacetamide) of a molecular weight of 30,000.

C. Hydrolysis of Poly(vinylacetamide) to Poly(vinylamine hydrochloride)

The poly(vinylacetamide) obtained in Part B (4.97 kg) was dissolved in 5.85 l of water with heating in a 50 l flask. Concentrated hydrochloric acid (5.85 l) was added and the resulting solution was stirred and heated at a gentle reflux (97°–106° C.) for 23 hours. A precipitate formed and was redissolved by addition of 1,170 ml of water. Reflux was continued and over the next 17 hours, 1,000 ml of water was added in several portions to maintain solubility of the polymer. After a total of 40 hours at reflux, the polymer was precipitated by the addition of 5.85 l of concentrated hydrochloric acid. A thick polymeric gum was isolated by decantation and dried under vacuum at 50°–100° C. with occasional pulverization for 56 hours to give 3.1 kg of poly(vinylamine hydrochloride) as a granular solid.

EXAMPLE II

Preparation of poly(N-methylvinylamine):

A. Formation of bis-acetylate

The preparation of poly(N-methylvinylamine) was begun by adding 250 g of N-methylaminoethanol to 691 g (2.20 equivalents) of acetic anhydride at 115°–120° C. The reaction was very exothermic (cooling required) and was complete by the time the addition was concluded. The bis-acetylated product,

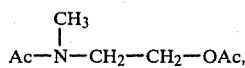

was isolated by vacuum distillation (bp 95°–98°/0.1 mm) as a colorless oil in 93% yield.

B. Pyrolyses of bis-acetylate

The bis-acetylated product of Step A was pyrolyzed by passing 642 g of this material at a rate of 1.17 g/min through a Pyrex ® helices-packed quartz tube (3.5 cm diameter, 40 cm length) maintained at 480°. A 400 ml/min argon stream was employed. The crude pyrolysate was a dark orange oil weighing 629 g. The crude mixture containing the desired N-methylvinylacetamide was distilled (72° C./20 mm) to afford 119 g (30%) of purified N-methylvinylacetamide.

C. Polymerization

Polymerization of 75 g of purified N-methylvinylacetamide was carried out in 150 ml of methanol at 70° C. in the presence of 4 mol % of AIBN. The polymerization was complete within 12 hours and afforded 72 g (96% yield) of poly(N-methylvinylacetamide).

D. Hydrolysis

The polymeric amide of Step C was hydrolysed with 6 N HCl at 125° to yield poly(N-methylvinylamine) as the hydrochloride. This material had a molecular weight of about 20,000 as determined by gel permeation chromatography comparisons to standards. The hydrolysis was monitored by NMR and required roughly 40 hours to go to completion. The product was isolated in essentially quantitative yield by precipitation of the partially evaporated reaction mixture from isopropanol.

EXAMPLES III AND IV

Preparation of high and low molecular weight poly(vinylamine hydrochloride):

The polymerization of vinylacetamide set forth in Step B of Example I was repeated twice on a smaller scale and varying reaction conditions to change the product molecular weight.

In Example III, the relative amount of AIBN polymerization catalyst was reduced by a factor of four, the reaction temperature was lowered to 63° C. and the reaction time was increased to 87 hours. The product was recovered as in Example I, Step B and found to have a molecular weight of 110,000. This material was hydrolyzed to poly(vinylamine) hydrochloride by the method of Example I, Step C.

In Example IV, the relative volume of isopropanol solvent employed was doubled. This reduced the average molecular weight of the poly(vinylacetamide) product to 20,000. The poly(vinylacetamide) was hydrolyzed to poly(vinylamine) in accordance with the process of Example I, Step C.

EXAMPLE V

Preparation of poly(α-methylvinylamine):

A. Preparation of 2-Amino,2-Cyano-Propane 85.1 g (1 mole) of acetone cyanohydrin is placed in a 2 l pressure vessel and the temperature is raised to 75° C. The pressure is raised to 25 psi with NH₃ gas and is maintained there until the pressure no longer drops (approximately 45 minutes). The crude product is then distilled to afford 46.5 g (0.55 mole, 55%) of product as a colorless oil, bp 58°–60°/20 mm.

B. Preparation of 2-Acetamido-2-Cyano-Propane 46.0 g (0.55 mole) of the aminonitrile is added to 67 g (1.20 equiv.) of Ac₂O with stirring at 80°. After 10 minutes the crude product is vacuum distilled to afford 55.9 g of a yellow solid, bp 115°/0.20 mm.

Recrystallization from benzene affords 48.3 g (0.38 mole, 70%) of cream colored needles.

C. Preparation of Isopropenyl Acetamide

Pyrolysis of the acetamido nitrile is carried out by passing 27.6 g (0.22 mmole) through a 4 mm Pyrex ® helix packed quartz column maintained at 600°. The column employed is 3.5 cm in diameter and 40 cm in length. The addition is carried out under a vacuum of 15 mm and the HCN generated is collected in a liquid N₂ trap. The product is 17.5 g of dark yellow solid. Distillation affords 10.4 g (0.10 mole, 48%) of product as a pale yellow crystalline solid, bp 72°–76°/0.20 mm.

D. Preparation of Polyisopropenyl Acetamide 5.0 g (43.9 mmole) of 89% pure isopropenyl acetamide is refluxed for 60 hours under Ar in 15 ml of MeOH containing 144 mg of AIBN. The product is isolated by precipitation from acetone to afford 1.39 g (28%) of a white powder. The molecular weight is 2,000.

E. Preparation of Polyisopropenyl Amine 300 mg (3.03 mmole) of the above material is refluxed for 24 hours in 20 ml of 6 N HCl under Ar. The reaction solvent is removed to afford 0.42 g of product. Analysis indicated it to be 73% deacetylated.

EXAMPLE VI

Preparation of Poly(N-butyl vinylamine):

A. Formation of bis-acetate 117 g (1 mole) of N-n-butylaminoethanol is treated with 225 g (2.2 mole) of Ac₂O at 100° for 4 hours. The bis-acetate is obtained by vacuum distillation in about 82% yield.

B. Pyrolysis of bis-acetate

The bis-acetate product of Step A is pyrolyzed by passing 100.5 g (0.5 mole) of this material at a rate of 1.25 g/min through a Pyrex ® helices-packed quartz tube (3.5 cm×40 cm) maintained at 495°. A 400 ml/min Ar stream is employed. The crude pyrolysate is a brownish-orange oil weighing 87.3 g. The crude mixture containing the desired N-n-butylvinylacetamide is distilled (96°/20 mm) to afford 30.3 g (43%, 0.22 mole) of product.

C. Polymerization

A sample of 25.0 g (0.18 mole) of purified vinylacetamide from Step B above is polymerized in 60 ml of MeOH at reflux in the presence of 4 mole % AIBN. The polymerization is complete within 18 hours and afforded 23 g (92%) of poly(N-n-butylvinylacetamide). The product is isolated by precipitation from ether and the molecular weight is determined to be about 38,000.

D. Hydrolysis

The polymeric amide of Step C is hydrolyzed with 10 parts by weight of 6 N HCl at 125°. The yield of poly(N-n-butylvinylacetamine) as the hydrochloride salt is quantitative. The hydrolysis, which is monitored by NMR, requires about 60 hours to reach completion. The product is isolated by precipitation of the partially evaporated reaction mixture from isopropanol.

EXAMPLE VII

Preparation of a Red Colorant:

A. Preparation of 1-nitro-2-methylanthraquinone

To a 1 liter flask was added 100 g (0.45 mole) of 2-methylanthraquinone and 500 ml of 96% $H_2SO_4$. The mixture was stirred until it was entirely homogeneous and then cooled to 0° C. The addition of 50.5 g (0.50 mole) of $KNO_3$ was then carried out in ten portions in such a way that the temperature did not rise above 5° C. This required two hours. A yellow product precipitated out after roughly half the $KNO_3$ had been added.

The yellow slurry was then stirred at 0° C. for 20 hours and poured into 12 l of ice/$H_2O$ with vigorous stirring. Stirring was stopped, the precipitate was allowed to settle, and the liquid was removed. The precipitate was washed with water until the pH of the wash water was pH 4-5.

An aqueous slurry of the precipitate (2.5 liters in volume) was placed in a 5 liter flask. 100 g of $Na_2SO_3$ were added and the mixture was heated and stirred at 95° C. for three hours. The slurry was filtered. The solids were washed with boiling $H_2O$ and sucked dry. The product was shown to be 1-nitro-2-methylanthraquinone.

B. Preparation of 1-amino-2-methylanthraquinone

The wet filter cake of 1-nitro-2-methylanthraquinone (0.45 mole) was placed in a 5 l flask. To the flask was added 420 g (1.75 mole) of $Na_2S.9H_2O$ dissolved in 2.5 l of $H_2O$ and the slurry was heated and then stirred at 95°–99° C. for 2 hours. The reaction mixture was filtered and the orangish-red solid 1-amino-2-methylanthraquinone product was washed with hot $H_2O$ until the filtrate was clear and dried in vacuo at 70° C.

C. Preparation of 1-amino-2-methyl-4-bromoanthraquinone

Into a 250 ml flask was added 10 g (42.2 mmole) of 1-amino-2-methylanthraquinone of Part B and 150 ml of glacial acetic acid. The mixture was heated to 35° C. and 8.44 g (52.8 mmole) of bromine was added in one portion. After stirring for 20 hours at 35° C., TLC ($CHCl_3$ on $SiO_2$) showed 10-20% of residual starting material still remaining.

An additional 1.69 g (0.25 equivalent) of $Br_2$ was added and the temperature was raised to 50° C. for 4 hours. TLC at this time indicated that the reaction was essentially complete.

The reaction mixture was cooled to room temperature and filtered. The solid product was washed with acetic acid (50 ml) and $H_2O$ (100 ml).

The wet filter cake was added to 500 ml of hot (80° C.) $H_2O$ containing 25 g of $NaHSO_3$ and stirred for 30 minutes at this temperature. The red solid 1-amino-2-methyl-4-bromoanthraquinone was recovered, washed and dried.

D. Preparation of 3'-carbethoxy-2-methyl-4-bromo-1,9-anthrapyridone

With magnetic stirring, two mmoles (630 mg) of the bromoanthraquinone prepared in Part C were treated with 4.02 g (26 mmole) of diethyl malonate and 9 mg of $Na_2CO_3$ for two hours at 180°–190° C. Volatiles were removed with an argon stream. After cooling, the product was filtered and the residue was washed with alcohol, hot water, and alcohol again and stirred overnight with 100 ml of toluene. After filtration and drying, the yield was 0.70 g (85%) of solid, 3'-carbethoxy-2-methyl-4-bromo-1,9-anthrapyridone, i.e.

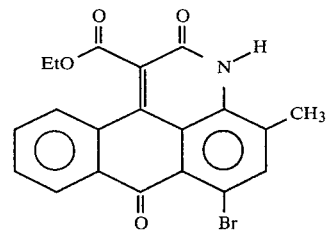

This material was not substantially soluble in water. Its solubility was estimated to be less than 50 ppm (basis water).

E. Preparation of a Polymeric Colorant

A 200-ml, one-neck flask was charged with 0.64 g (8 mmol) of the poly(vinylamine hydrochloride) prepared in Example I, 3.4 g (32 mmol) of $Na_2CO_3$, and 75 ml of $H_2O$. The mixture was stirred until a homogeneous solution (pH 10.7) was obtained and 25 ml of pyridine was added. Then, 1.64 g (4 mmol) of 3'-carbethoxy-2-methyl-4-bromoanthrapyridone, prepared in Step D, was added along with 143 mg (1 mmol) of red $Cu_2O$ and the mixture was lowered into a bath pre-heated to 120° C. and stirred vigorously at reflux for 30 minutes.

The reaction mixture was filtered, while still boiling hot, through a sintered glass filter and the small amount of residue was washed with 100 ml of $H_2O$-pyridine (3:1). A clear solution (200 ml, pH 10.8) of the following red polymeric dye in 3:1 water-pyridine was obtained.

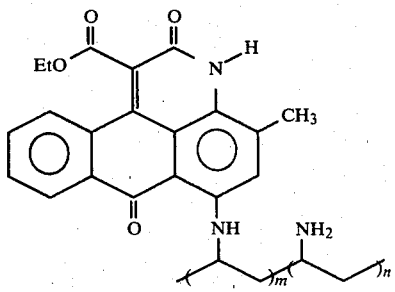

The solution was divided into two equal portions with one portion being purified as is described in Step G below, and the other half being purified as is described in Step H.

F. Preparation Of Nonsolubilized Colorant By Dialysis

One-half (100 ml) of the solution obtained in Step E was placed in a regenerated cellulose dialysis bag (average pore radius 24 Å, estimated molecular weight cutoff $2 \times 10^4$) and dialyzed against 4 liters of 25% aqueous pyridine for 72 hours. Following this, dialysis was carried out against 25% aqueous pyridine that was 0.5% by weight NaCl until the polymer completely precipitated (~10 days). Dialysis was then carried out against dilute saline solution (72 hours) and finally against pure $H_2O$ (24 hours). After centrifugation (8000 rpm for one hour) and drying, there was obtained 700 mg of polymeric dye as a fine red powder. This polymeric dye was soluble in water at pHs of from about 2.0 to about 4.0, but otherwise was not substantially water-soluble. n and m were calculated as being equal, i.e., n=m based on feed ratios. By elemental analysis, m was seen to equal 0.95n.

G. Purification Of Nonsolubilized Colorant By Ultrafiltration 100 ml of the solution obtained in Step F was ultrafiltered with an Amicon Model 202 stirred cell (Amicon Corp., Lexington, Mass.) employing a 62 mm diameter PM 10 membrane (molecular weight cutoff $1 \times 10^4$). The device was operated at 40 psi Ar pressure. Ultrafiltration was carried out with 2.9 liters (29 diavolumes) of 15% aqueous pyridine made up to 0.02 N in NaOH (pH 12). After ultrafiltration the solution was precipitated onto 50 g of Celite ® which was in 1 liter of rapidly stirred isopropyl alcohol containing 5 ml of acetic acid. The Celite was filtered, washed with isopropyl alcohol (2×200 ml) and dried.

The dye was extracted from the Celite by a two-fold treatment (stirred 30 minutes) with 200 ml of $H_2O$ containing approximately 10 ml of 12 N HCl (pH 2.0). Filtration of the Celite followed by partial evaporation of the solution (pH maintained at 2-3 by the addition of HCl as necessary) and lyophilization provided 540 mg of polymeric dye.

EXAMPLE VIII

Preparation of a red colorant:

A. Coupling Of Chromophores

To a solution of 1.87 g (70 mmol-1 equivalent) of the poly(N-methylvinylamine hydrochloride) prepared in Example II, in aqueous ethylene glycol (2:1 glycol/water) containing 4 equivalents of $Na_2CO_3$, was added ½ an equivalent of the 3'-carbethoxy-2-methyl-4-bromo-1,9-anthrapyridone prepared in Step D of Example VII and 0.2 g of red $Cu_2O$. The reaction was completed in 1.5-2 hrs at 110° C. The catalyst and other solid contaminants were removed by filtration to yield a solution of the coupled colorant

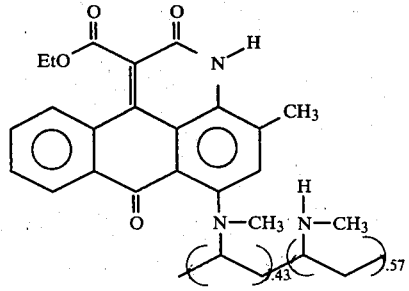

B. Workup

The dye was purified in a manner identical to that of Example VII, Part H. The yield of red polymeric product was 3.67 g. Elemental analysis showed m=0.43 and n=0.57.

EXAMPLE IX

A. Preparation of 3'-acetyl-2-methyl-4-bromo-1,9-anthrapyridone

A 100 ml flask was charged with 3.6 g (10 mmole) of the 1-amino-2-methyl-4-bromoanthraquinone of Part C of Example VII, 10 ml (10.2 g, 78.5 mmoles) of ethyl acetoacetate and 0.033 g (0.31 mmole) of sodium carbonate. The mixture was heated under a slow argon flow in a 180°-190° C. oil bath with stirring. Lower boiling materials ($H_2O$, EtOH, etc.) were distilled off as they were produced. After heating for 1.5 hours, a thin layer chromatogram (silica gel, ethyl acetate) indicated the reaction was complete. The reaction mixture was cooled and filtered. The residue was washed with ethanol, hot water, and ethanol; then the residue was stirred with boiling toluene for 5 minutes and filtered. This process was repeated four times and the final residue was dried in a 44° C. vacuum oven overnight to yield 3.32 g (87% yield) of 3'-acetyl-2-methyl-4-bromo-1,9-anthrapyridone, i.e.,

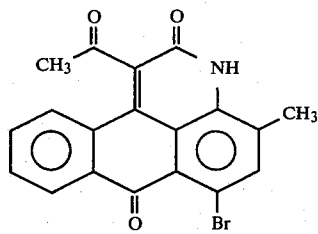

B. Coupling Of Dye Chromophore To A Polymer

A 250-ml, one-neck flask was charged with 0.64 g (8 mmol) of the poly(vinylamine hydrochloride) of Example III, 3.4 g (32 mmol) of $Na_2CO_3$, and 75 ml of $H_2O$. The mixture was stirred until a homogeneous solution (pH 10.7) was obtained. The solution was then treated with 25 ml of pyridine, 1.53 g (4 mmol) of 3'-acetyl-2-methyl-4-bromoanthrapyridone prepared in Step A of this Example, 143 mg (1 mmol) of red $Cu_2O$ and lowered into a bath preheated to 120° C.

After refluxing 30 minutes, the reaction mixture was filtered while still boiling hot and the trace of residue washed with 100 ml of 25% aqueous pyridine. This afforded a bright red solution of polymeric dye of the formula

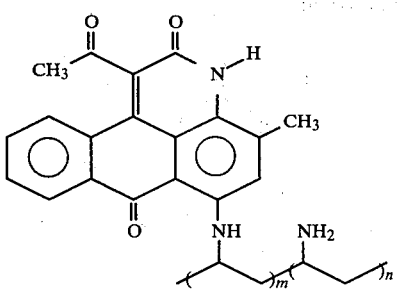

C. Purification

The 200 ml of polymeric dye solution (pH 11.5) were purified by ultrafiltering (9.0 liters of pH 12 15% aqueous pyridine), precipitating onto Celite, washing, and re-extracting into pH 2 H$_2$O as described in Example VII, Step G. After lyophilization, there was obtained 480 mg of product. Elemental analysis showed m=0.33 and n=0.67.

EXAMPLE X

A. Preparation of N-Acetyl-1-Methylamino-4-Bromoanthraquinone

A 250 ml flask equipped with a mechanical stirrer was charged with 30 g (95 mmole) of 1-methylamino-4-bromoanthraquinone (purchased from Sandoz), 19.5 g (191 mmole) of acetic anhydride, and 0.23 g of 96% H$_2$SO$_4$. The sludgelike mixture was heated and stirred at 110° for 30 minutes. The reaction mixture was cooled to 0° and 50 ml of H$_2$O was added. After stirring ½ hour, 55 ml of 30% NaOH was added and the entire mixture was then transferred to a pressure reactor for the following reaction. A TLC (EtOAc) showed only a single product in the reaction.

B. Preparation of 1'-Methyl-4-Bromoanthrapyridone

The acetyl anthraquinone from Part A was placed in a pressure vessel and heated and stirred at 120° for 2 hours. The reaction mixture was cooled, filtered, and washed with H$_2$O. After oven drying, the brown solid was dissolved in 200 g of 96% H$_2$SO$_4$ and reprecipitated by the addition of 40 ml of H$_2$O. The solid was filtered and washed with 25 g of 78% H$_2$SO$_4$. The filter cake was then stirred with 800 ml of H$_2$O, filtered, washed, and dried in vacuo. The solid then obtained was twice recrystallized from trichloroethane to afford 8.5 g of pure anthrapyridone.

C. Polymer Attachment Step

A 250 ml round bottomed flask was charged with 480 mg (6.0 mmole) of poly(vinylamine) of Example I, 2.54 g (24.0 mmole) of Na$_2$CO$_3$, and 36 ml of H$_2$O. The mixture was stirred until solution was complete and 72 ml of ethylene glycol was added. Then, 510 mg (1.50 mmole, 0.25 equivalents) of 1'-methyl-4-bromoanthrapyridone was added along with 50 mg of Cu$_2$O. The reaction mixture was then placed in a pre-heated oil bath, refluxed for ten minutes, and rapidly filtered. The red polymeric dye obtained in the filtrate is of the following composition.

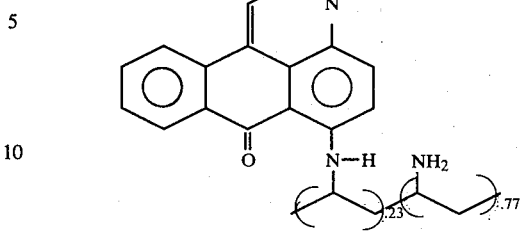

D. Workup

Purification was carried out by bag dialysis as described in Example VII, Step G. The yield of product was 0.57 g. Elemental analysis showed m=0.23 and n=0.77.

EXAMPLE XI

Preparation of a blue polymeric dye:

A. Coupling Of Dye To Polymer

A 250-ml, 3-neck flask, equipped with overhead stirrer, reflux condenser, Ar bubbler, and thermometer, was charged with 1.19 g (15 mmol) of poly(vinylamine hydrochloride) prepared in Example I and 50 ml of H$_2$O. The mixture was stirred until homogeneous and then treated with 0.60 g (15 mmol) of NaOH and 1.6 g (15 mmol) of Na$_2$CO$_3$. The mixture was stirred under Ar until homogeneous (pH 12.6) and then treated with 0.476 g (1.5 mmol) of 1-methylamino-4-bromoanthraquinone,

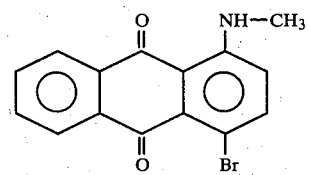

prepared according to C. V. Wilson, Org. Syn., 29, 68 (1949), and 10 mg of Cu$_2$Cl$_2$ as a slurry in 30 ml of pyridine. The reaction mixture was thoroughly deoxygenated with Ar and immersed in a preheated oil bath and refluxed under Ar.

The following treatments were made to the refluxing reaction mixture at the total elapsed times (based on attainment of reflux) indicated:

(a) 60 min., 1.50 mmol bromoanthraquinone, 20 ml pyridine;

(b) 120 min., 1.50 mmol bromoanthraquinone, 5 mg Cu$_2$Cl$_2$, 10 ml pyridine;

(c) 180 min., 1.50 mmol bromoanthraquinone, 10 ml pyridine, 0.25 ml (3 mmol) of 12 N NaOH;

(d) 240 min., 1.50 mmol bromoanthraquinone, 5 mg Cu$_2$Cl$_2$, 15 ml pyrydine;

(e) 300 min., 0.75 ml (3 mmol) of 12 N NaOH.

A total of 7.5 mmol of anthraquinone was added and the total volume of the reaction mixture was 135 ml (pyridine: H$_2$O/85:50). After 360 minutes, TLC (CHCl$_3$ on SiO$_2$) showed that no starting material remained. The polymeric blue colorant was filtered while still boiling not through a sintered glass filter and purified as described in Step B.

B. Purification

Without allowing the solution to cool, the dye was precipitated as rapidly as possible into one liter of rapidly stirred ice-cold acetone containing 20 g of Celite. After stirring ten minutes, the dyed Celite was filtered and washed with acetone (4×300 ml). The filtrates contained monomeric species and inorganic salts.

The blue polymeric dye was extracted from the Celite by eight consecutive treatments with one liter of dilute aqueous HCl (pH 2.5). After concentration (HCl added as needed to maintain the pH at 3.0), the solution was freeze-dried to provide 2.06 g of cationic polymeric blue dye. Elemental analysis of the material showed that m=0.48 and n=0.52 such that the product was

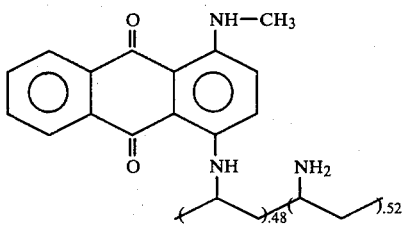

EXAMPLE XII

Preparation of a purple polymeric colorant:
A. Preparation of Chromophore

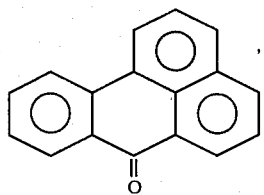

Benzanthrone, was vacuum sublimed. A 12.1 g portion (52.7 mmoles) was placed in a flask and dissolved in 50 ml of acetic acid with warming. 9.3 g of neat bromine was added along with 65 ml of additional acetic acid and 30 ml of nitrobenzene. The mixture was stirred and gradually heated—finally being maintained at 90° C. for 12 hours. The reaction mixture has become homogeneously yellow. The mixture was cooled and poured into a liter of water and 500 ml of dichloromethane to yield two phases. The color went to the organic phase which was isolated, dried with Na$_2$SO$_4$, filtered and evaporated to yield a solid chromophore which upon analysis was found to be:

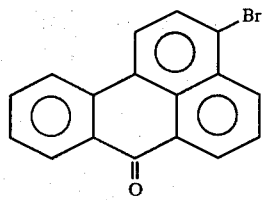

B. Coupling 358 mg (3.81 mmole, 1 equivalent) of the poly(N-methylvinylamine hydrochloride) of Example II and 10 ml of water and 25 ml of ethylene glycol are placed in a 100 ml flask. 1.62 g (15.2 mmole) of sodium carbonate, 0.5 g (0.42 equivalents) of the chromophore of Part A, and 50 mg of a cupric acetate catalyst are added and the mixture is heated to 110° C. and there maintained for 2-3 hours. Solids are removed by filtration to yield a clear ethylene glycol/water solution of the purple colorant

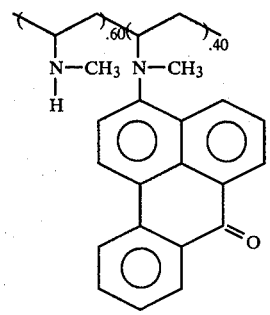

C. Workup

The product is isolated by precipitation onto Celite and extraction into dilute acid as described in Example XI, Step B. The yield of purple polymer is 0.45 g after lyophilization.

EXAMPLE XIII

Preparation of a polymeric orange colorant:
A. Preparation of Chromophore

Using the general method disclosed in Patki et al., *Indian Journal of Technology*, Vol. 12 (1974) p 540–545, 31.6 g (100 mmole) of the anthraquinone product of Example VII, Step C, is suspended in 100 ml of water. Sodium hydroxide (15 g in 60 ml of water) is added with stirring followed by 70 g (1.2 mole) of acetone. The mixture is refluxed for 20 hours. A TLC test indicates that the anthraquinone and acetone have reacted to completion. The mixture is cooled, neutralized with hydrochloric acid, and filtered to recover the yellow precipitate of 2,4-dimethyl-6-bromopyridinanthrone

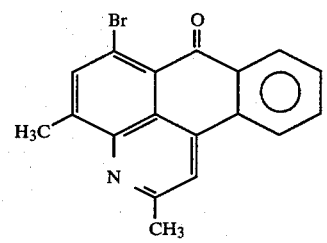

which is washed with water and dried.

B. Coupling

A 100 ml flask is charged with 0.64 g (8 mmole) of the poly(vinylamine hydrochloride) of Example III, 3.4 g (32 mmole) of Na$_2$CO$_3$, 32 ml of water, and 65 ml of ethylene glycol. Then 1.02 g (3.0 mmole) of the product of Step A, along with a catalyst consisting of 0.25 g of finely powdered cuprous oxide is added and the mixture is stirred at 100°–110° C. for 30 minutes. The reaction mixture is filtered to remove solids and yield an orange glycol/water solution of the polymeric colorant:

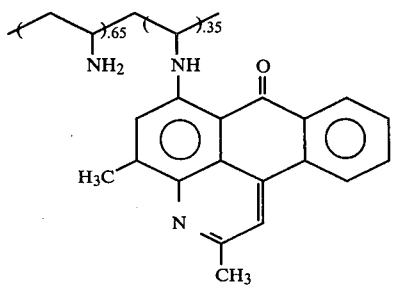

C. Workup

The product was purified by bag dialysis vs. aqueous pyridine as described in Example VII, Step G. The yield of polymer as a yellow powder, after filtration and drying, was 0.85 g.

EXAMPLE XIV

A. Chromophore preparation 1-amino-4-bromoanthraquinone, acetoacetic acid ethyl ester and alkane sulfonic acid catalyst are reacted in accordance with the teachings of Example 1 of U.S. Pat. No. 2,759,940 issued Aug. 21, 1956 to Bucheler et al., (which patent is herein expressly incorporated by reference) to yield the yellow chromophore

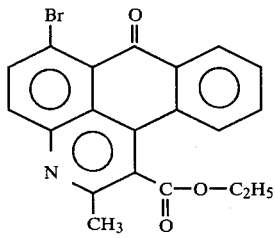

B. Coupling of Chromophores to Backbone 0.37 g (4 mmole) of the poly(isopropenylamine) hydrochloride prepared in Example V is dissolved in 48 ml of 2:1 ethylene glycol/water along with 1.70 g of $Na_2CO_3$. Then, 0.79 g (2 mmole) of the chromophore of Step A is added along with 0.3 g of cupric acetate monohydrate catalyst. The mixture is heated at 100° C. for 40 minutes.

The reaction mixture is filtered to remove solid residues and yield a solution of the yellow polymeric colorant

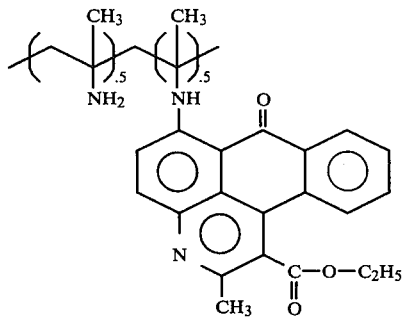

C. Workup

The product was precipitated by addition to one liter of rapidly stirred acetone containing 20 g of Celite. Thorough extraction of the celite with dilute HCl (pH 3.0), followed by evaporation and freeze-drying, afforded 0.75 g of polymeric yellow colorant.

EXAMPLE XV

A. Preparation of Chromophore 4.4 g (10 mmole) of D&C Orange #4,

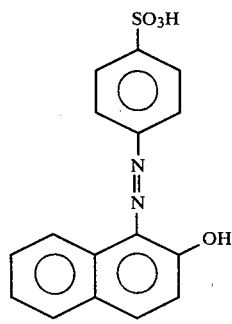

is reacted overnight at room temperature with an excess of acetic anhydride in pyridine to acetylate the naphthyl hydroxyl group. The acetylated product is recovered, and added to a solution of one equivalent thionyl chloride in 100 ml of benzene containing a catalytic amount of DMF. After stirring for 2 hours at room temperature, the bright orange chlorosulfonyl derivative,

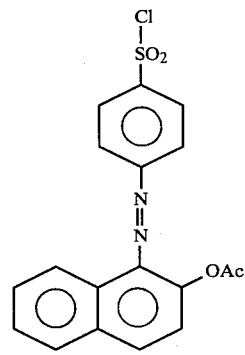

is recovered.

B. Coupling of Chromophore to Backbone 7.0 g of the poly(vinylamine hydrochloride) prepared in Example IV is added to a 2000 ml flask, 700 ml of water and 350 ml of tetrahydrofuran are added and the pH is raised from 2.5 to 9.5 by addition of 2.5 N NaOH.

Next 13.7 g (0.4 equivalents, based on total amine polymer) of the chromophore of Part A is slowly added at room temperature while maintaining the pH at 9.0–9.5 by NaOH addition. Additional THF and NaOH are added and the pH is maintained at 9.5–10.5. A final stirring is carried out at pH 12.5–13.0 to complete hydrolysis of the acetyl group. The product is not isolated, but is used immediately for Step C.

C. Workup

All THF was removed by evaporation at reduced pressure to provide a pH 13.0 solution of the following anionic dye.

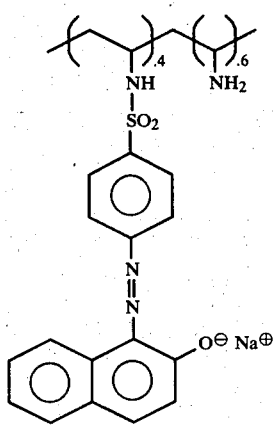

Ultrafiltration of this solution was then carried out with 15% aqueous pyridine made up to 0.02 N in NaOH (pH 12.0). Roughly 10 diavolumes were required to remove the monomeric impurities. The solution was then precipitated onto 200 g of Celite which was in 10 liters of rapidly stirred acetone containing 100 ml of acetic acid. The Celite was filtered, washed with acetone (4×1 liter), and dried.

The dye was extracted from the Celite by five one-hour treatments with 2 liters of dilute HCl (pH 2.0). Evaporation of the solution (pH maintained at 2-3 by the addition of HCl as necessary) and lyophilization provided 15.5 g of brilliant orange polymeric dye.

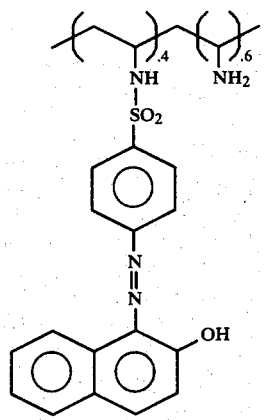

EXAMPLE XVI

A. Preparation of Chromophore 1. 3'-Carbethoxy-2-Bromo-4-p-Toluidinoanthrapyridone 31.4 g (77.1 mmoles) of 1-amino-2-bromo-4-p-toluidinoanthraquinone (Benzenoid Organics Inc.), 250 ml of diethylmalonate, and 0.63 g of sodium acetate were heated at 180°-185° under an argon stream for 105 minutes. During this period the reaction mixture turned from deep blue to purplish red. The reaction mixture was cooled to 45° and the excess diethylmalonate was removed in vacuo (0.25 mm). The product was dried at 80°/0.1 mm for 18 hours and had the following structure:

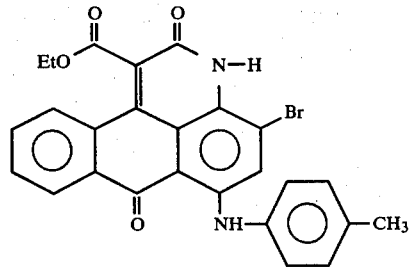

2. Potassium 3'-Carbethoxy-4-p-Toluidinoanthrapyridone-2-Sulfonate

The crude product from the above reaction (38.8 g, 77.1 mmoles) was refluxed with 40.0 g of $K_2SO_3$ in $H_2O/\phi OH$ (3:7). The course of the reaction was followed by TLC (5% $MeOH/CHCl_3$ elution on silica gel). After 48 hours, the reaction was judged complete. The phenol was removed with steam, at which point the product precipitated. The royal purple product was filtered and dried in vacuo to afford 39.7 g of monomeric dye of the following structure:

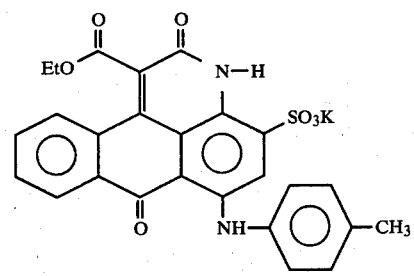

3. 3'-Carbethoxy-4-p-Toluidinoanthrapyridone-2-sulfonyl Chloride 3.90 g (7.2 mmole) of the above anthrapyridone sulfonate, 83.5 g (0.71 mole) of thionyl chloride, and 25 drops of DMF were stirred at room temperature for 7 days in 100 ml of 1,1,2,2-tetrachloroethane. The excess reagent and solvent were removed by vacuum distillation and the purple residue was dissolved in methylene chloride and filtered to remove KCl. Removal of the solvent and drying in vacuo afforded a quantitative yield (3.76 g) of sulfonyl chloride.

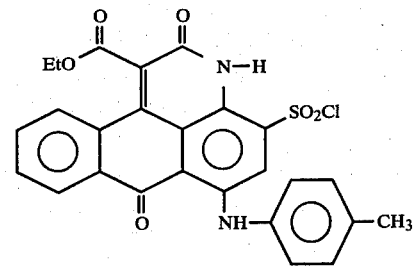

B. Chromophore Attachment (Schotten-Bauman Reaction)

318 mg (4.0 mmoles) of poly(vinylamine) hydrochloride (prepared in Example I) was dissolved in 15 ml of $H_2O$ and the pH was raised to 10.0 by the addition of 10% NaOH solution. To the solution was added 349 mg (0.66 mmole) of the anthrapyridone sulfonyl chloride of Part A and 5 ml of ethylene glycol. These additions were repeated twice more over a period of 7.5 hours as the pH was maintained at 9.5–10.5 by the addition of NaOH, as necessary.

C. Workup

The product of this reaction is isolated as follows.

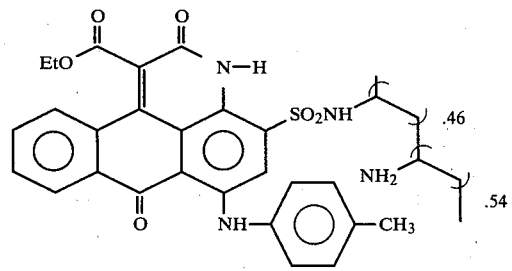

The alkaline aqueous glycol mixture was diluted to a volume of 100 ml with 15% aqueous pyridine made up to 0.02 N with NaOH (pH 12.0) and ultrafiltered with an Amicon Model 202 stirred cell utilizing a PM 10 membrane (molecular weight cutoff $1 \times 10^4$). After the ultrafiltration had been carried to 10 diavolumes (1.0 liter) with this pyridine solution, the deep purple mixture was precipitated into one liter of rapidly stirred isopropyl alcohol containing 50 g of Celite and 5 ml of acetic acid.

The dye was extracted from the Celite by two 30 minute treatments with 250 ml of H$_2$O made to pH 2.0 with HCl. This afforded, after lyophilization, 514 mg of royal purple polymer shown by elemental analysis to have m=0.46 and n=0.54.

EXAMPLE XVII

A. Preparation of Chromophore 1. 3'-Carbethoxy-2-methyl-4-anilinoanthrapyridone 4.12 g (10 mmole) of 3'-carbethoxy-2-methyl-4-bromoanthrapyridone (purchased from Sandoz Colors and Chemicals) was stirred under an inert atmosphere with 25 ml of aniline in a bath maintained at 145°–150°. After 2.5 hrs, TLC (EtOAc on silica gel) indicated the complete disappearance of starting material with the formation of a sole product. Removal of the excess aniline by vacuum distillation followed by drying in vacuo (100°/0.1 mm) afforded a quantitative yield of product (4.24 g).

2. Chlorosulfonation 4.00 g (9.43 mmole) of 3'-carbethoxy-2-methyl-4-anilinoanthrapyridone was dispersed in 25 ml of CHCl$_3$ and the mixture was cooled to 0°. To the mixture was added dropwise over a period of 1 hr 5 equivalents (4.10 g) of chlorosulfonic acid. After stirring at 0° for an additional 1 hr, the reaction mixture was filtered and the product was washed well with CHCl$_3$ (0°) and then dried in vacuo to afford 4.66 g (8.91 mmoles) of sulfonyl chloride as a violet-red crystalline solid. Elemental analysis confirms the following structure:

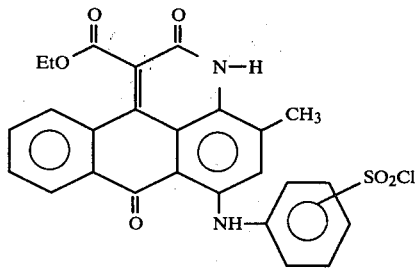

B. Coupling 523 mg (1.0 mmole) of the above sulfonyl chloride was treated with 3.0 mmoles (238.5 mmoles) of poly(vinylamine) in 40 ml of THF-H$_2$O (1:3) at room temperature and pH 10.5–11.0. This afforded a red polymeric dye with poor water solubility of the following structure:

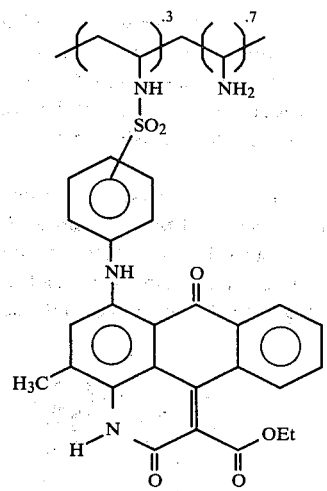

C. Workup

The THF was removed from the bright red dye solution by rotary evaporation and the mixture was then diluted to a volume of 100 ml with 15% aqueous pyridine made up to 0.02 N with NaOH. The mixture was ultrafiltered to a total of 15 diavolumes (1.5 liters) of this pyridine solution and then precipitated onto 65 g of Celite in 1.5 liters of rapidly stirred isopropyl alcohol containing 25 ml of acetic acid.

Extraction of the dye from the Celite was carried out by two 30 minute treatments with 500 ml of H$_2$O made to pH 3.0 with HCl. This afforded, after evaporation and freeze-drying, 643 mg of bright red polymeric dye shown by elemental analysis to have m=0.30 and n=0.70.

EXAMPLES XVIII AND XIX

The preparation of Example VIII is repeated twice varying the backbone employed. In Example XIX, 1.1 equivalent of poly(N-butylvinylamine), as prepared in Example VI, is employed as backbone. In Example XX, poly(α-methylvinylamine), as prepared in Example X, is employed as backbone.

EXAMPLE XX

A. Preparation of 3'-carboethoxy-2'-methyl-2-methyl-4-bromo-1,9-anthrapyridine

Following the teachings of Bücheler and Peter in U.S. Patent No. 2,759,940 (cited previously in Example XIV, Step A), 15.8 g (50 mmol) of 1-amino-2-methyl-4-bromoanthraquinone (Example 7, Step C) were heated for three hours at 135°–140° C. with 178.5 g (1.37 mol) of acetoacetic ester and 1.0 ml of methane sulfonic acid. During the course of the reaction, volatiles were removed with a slow stream of Ar. After cooling, the reaction mixture was diluted with ethanol (100 ml), filtered, and the residue washed with ethanol to provide 17.9 g of the following bromoanthrapyridine as a dark brown powder.

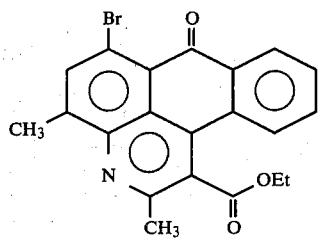

B. Preparation of an Orange Dye

A 250-ml, three-neck flask, equipped with overhead stirrer, reflux condenser, Ar bubbler, and thermometer, was charged with 1.19 g (15.0 mmol) of poly(vinylamine hydrochloride) prepared in Example I, 0.60 g (15 mmol) of NaOH, 1.60 g (15 mmol) of $Na_2CO_3$, and 50 ml of $H_2O$. The mixture was stirred until a homogeneous solution was obtained (pH 12.6), at which point the solution was treated with 615 mg (1.50 mmol) of the anthrapyridine prepared in Part A, 10 mg of $Cu_2Cl_2$, and 30 ml of pyridine. The reaction mixture was lowered into a pre-heated bath and stirred at reflux under Ar.

The following treatments were made to the reaction at the times indicated:

(a) 60 minutes, 1.5 mmol bromoanthrapyridine, 20 ml pyridine;

(b) 120 minutes, 1.5 mmol bromoanthrapyridine, 5 mg $Cu_2Cl_2$, 10 ml pyridine, 0.25 ml (3 mmol) of 12 N NaOH;

(c) 210 minutes, 1.5 mmol bromoanthrapyridine, 10 ml pyridine;

(d) 300 minutes, 1.5 mmol bromoanthrapyridine, 5 mg $Cu_2Cl_2$, 20 ml pyridine, 0.25 ml (3 mmol) of 12 N NaOH.

After 390 minutes, the reaction mixture was filtered through a sintered funnel while still hot and immediately diluted with 160 ml of boiling pyridine.

C. Workup

The 300 ml of deep orange solution (pyridine: $H_2O$, 5:1, pH 12.9) was added as rapidly as possible (no cooling) to 2.5 liters of rapidly stirred ice-cold acetone containing 50 g of Celite. After stirring 15 minutes, the celite was filtered and washed with acetone (4×500 ml). The filtrate was examined by TLC and was shown to contain principally monomeric species.

The orange polymeric dye was extracted from the Celite by eight consecutive treatments with one liter of dilute aqueous HCl (pH 3.4). This afforded, after lyophilization, 2.34 g of cationic orange dye. Elemental analysis showed that m=0.42 and n=0.58.

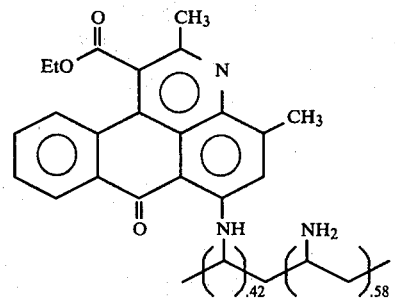

EXAMPLE XXI

A. Preparation of a Blue Dye

A 250-ml, 3-neck flask, equipped with overhead stirrer, reflux condenser, Ar bubbler, and thermometer, was charged with 1.19 g (15 mmol) of poly(vinylamine hydrochloride) prepared in Example I, 0.6 g (15 mmol) of NaOH, 1.6 g (15 mmol) of $Na_2CO_3$, and 50 ml of $H_2O$. The solution was stirred until homogeneous (pH 12.5) and then treated with 476 mg (1.5 mmol) of 1-amino-2-methyl-4-bromoanthraquinone (Example VII, Step C), 10 mg of $Cu_2Cl_2$, and 30 ml of pyridine. The mixture was lowered into a preheated bath (125° C.) and stirred at reflux under Ar.

The following treatments were made to the reaction mixture at the times indicated:

(a) 60 minutes, 1.5 mmol bromoanthraquinone, 20 ml pyridine;

(b) 120 minutes, 1.5 mmol bromoanthraquinone, 5 mg $Cu_2Cl_2$, 10 ml pyridine;

(c) 210 minutes, 1.5 mmol bromoanthraquinone, 10 ml pyridine, 0.25 ml (3 mmol) of 12 N NaOH;

(d) 300 minutes, 1.5 mmol bromoanthraquinone, 5 mg $Cu_2Cl_2$, 20 ml pyridine, 0.25 ml (3 mmol) of 12 N NaOH.

A TLC ($CHCl_3$ on $SiO_2$) after 390 minutes showed that almost no 4-bromoanthraquinone remained. The mixture was filtered while still boiling hot through a fritted filter and diluted with 160 ml of boiling pyridine.

B. Purification

Without allowing the dye solution to cool, the deep blue solution was precipitated into 2.5 liters of rapidly stirred ice-cold acetone containing 50 g of celite. After stirring for 15 minutes, the celite was filtered and washed thoroughly with acetone (4×500 ml). The purplish filtrate contained (TLC analysis) primarily 1-amino-2-methyl-4-hydroxyanthraquinone and a trace of 1-amino-2-methyl-4-bromoanthraquinone which remained unreacted.

The blue polymeric dye was extracted from the celite by ten consecutive 30 minute treatments with one liter of dilute aqueous HCl (pH 2.5). Lyophilization provided 1.98 g of cationic blue polymeric dye. Elemental analysis showed than m=0.44 and n=0.56.

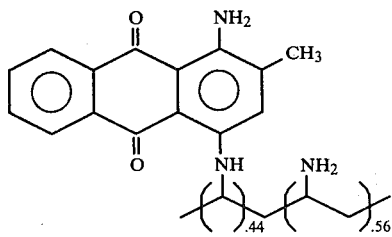

EXAMPLE XXII

A. Preparation of 3'-phenyl-2-methyl-4-bromo-1,9-anthrapyridone

A 250-ml flask, equipped with overhead stirrer, condenser, and Ar inlet was charged with 15.8 g (50 mmol) of 1-amino-2-methyl-4-bromoanthraquinone (Example VII, Step C) and 120 ml of toluene. The mixture was treated with phenylacetyl chloride (8.5 g, 55 mmol) and heated to reflux. After 3.5 hours, the mixture was cooled to 80° and filtered. The filtrate was evaporated to 30 ml and cooled. The deposited dark yellow crystals were filtered, washed with diethylether, and dried to afford 12.5 g of N-phenylacetyl anthraquinone.

This material (4.56 g, 10.5 mmol) was placed in a 100-ml, 3-neck flask equipped with condenser, overhead stirrer, thermowell, and Ar inlet. After 30 ml of 2-methoxyethanol were added, the contents were heated to 122° C. and 0.45 g (8 mmol) of KOH in 0.6 ml of $H_2O$ was added dropwise over 60 seconds. After stirring for one hour at 120° C., the mixture was cooled to 5° C. and the solid obtained (1.71 g) was filtered. Concentration of the mother liquor and recrystallization of the residue from acetic acid (170 ml) afforded an additional 2.30 g of product. The total yield of anthrapyridone was 4.01 g.

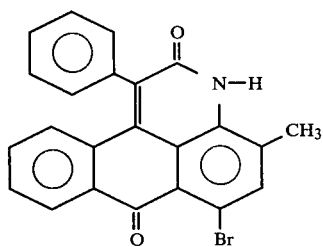

B. Preparation of a Red Polymeric Dye

A 200-ml, one-neck flask was charged with 0.64 g (8 mmol) of poly(vinylamine hydrochloride) prepared in Example I, 3.4 g (32 mmol) of $Na_2CO_3$, and 75 ml of $H_2O$. The mixture was stirred until a homogeneous solution (pH 10.7) was obtained. 25 ml of pyridine and 1.67 g (4 mmol) of 3'-phenyl-2-methyl-4-bromoanthrapyridone prepared in Step A were added along with 143 mg (1 mmol) of red $Cu_2O$ and the mixture was lowered into a bath preheated to 120° C. and stirred vigorously at reflux for 180 minutes. The reaction mixture was filtered while still boiling hot and diluted with 100 ml of 15% aqueous pyridine made up to 0.02 N in NaOH.

C. Purification

The red polymeric dye solution (200 ml, pH 12.0) obtained in Step B

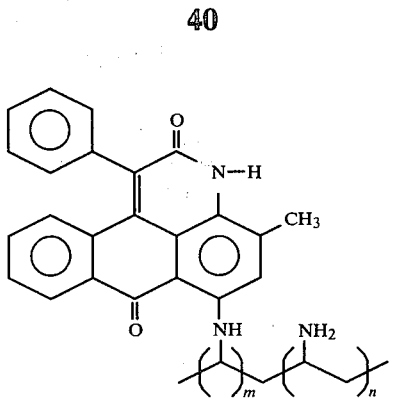

was ultrafiltered with an Amicon Model 202 stirred cell in conjunction with a PM 10 membrane (molecular weight cutoff $1 \times 10^4$). Ultrafiltration was carried out with 4.0 liters (20 diavolumes) of 15% aqueous pyridine made up to 0.02 N with NaOH. The red dye solution was then precipitated onto 100 g of celite which was in 2 liters of rapidly stirred isopropyl alcohol containing 10 ml of acetic acid. The celite was filtered, washed with isopropyl alcohol (2×400 ml), and dried.

The dye was extracted from the celite by two treatments with 500 ml of dilute aqueous HCl (pH 2.0). This afforded, after freeze-drying, 1.23 g of red polymeric dye. Elemental analysis showed m=0.48 and n=0.52.

EXAMPLE XXIII

A. Preparation of 3'-carbethoxy-2'-methoxy-2-methyl-4-bromo-1,9-anthrapyridine

A 500-ml, 3-neck flask, equipped with overhead stirrer, thermometer, and Ar bubbler, was charged with 4.12 g (10 mmol) of 3'-carbethoxy-2-methyl-4-bromoanthrapyridone prepared in Example VII, Step D, and 200 ml of dry N,N-dimethylformamide. Stirring was begun and the mixture was heated to 40° and thoroughly deaerated with Ar. The mixture was then treated with 1.38 g (10 mmol) of anhydrous $K_2CO_3$ and 6.30 g (50 mmol) of dimethyl sulfate and stirring was continued at this temperature under Ar.

The reaction was followed by TLC (EtOAc on $SiO_2$) which showed the clean formation of a single product. After 72 hours the reaction mixture was poured into 1.4 liters of well stirred water and, after stirring five minutes, the product was allowed to settle. Decantation, followed by filtration and water washing, provided 3.76 g (8.8 mmol) of methoxyanthrapyridine. The structure of the product was determined by nuclear magnetic resonance spectroscopy, infrared spectroscopy, ultraviolet spectroscopy, and elemental analysis.

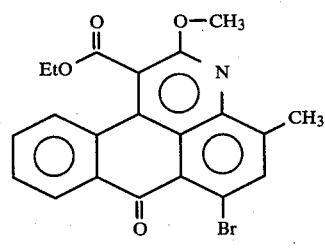

B. Preparation of an Orange Polymeric Dye

A 250-ml, 3-neck flask, equipped with overhead stirrer, reflux condenser, Ar bubbler, and thermometer, was charged with 1.19 g (15 mmol) of poly(vinylamine hydrochloride) prepared in Example I, 0.6 g (15 mmol) of NaOH, 1.6 g (15 mmol) of $Na_2CO_3$, and 50 ml of $H_2O$. The mixture was stirred until a homogeneous solution was obtained (pH 12.6), at which point the solution was treated with 639 mg (1.50 mmol) of the methoxyanthrapyridine prepared in Part A, 10 mg of $Cu_2Cl_2$, and 30 ml of pyridine. The mixture was lowered into a pre-heated bath (125°) and stirred at reflux under Ar.

The following treatments were made to the reaction at the times indicated:

(a) 60 minutes, 1.5 mmol methoxyanthrapyridine, 20 ml pyridine;

(b) 120 min, 1.5 mmol methoxyanthrapyridine, 5 mg $Cu_2Cl_2$, 10 ml pyridine, 0.25 ml (3 mmol) of 12 N NaOH;

(c) 210 minutes, 1.5 mmol methoxyanthrapyridine, 10 ml pyridine;

(d) 300 minutes, 1.5 mmol methoxyanthrapyridine, 5 mg $Cu_2Cl_2$, 20 ml pyridine, 0.25 ml (3 mmol) of 12 N NaOH.

After 390 minutes the reaction mixture was filtered through a fritted funnel while still boiling hot and immediately diluted with 160 ml of boiling pyridine.

C. Workup

The 300 ml of deep orange solution (pyridine:$H_2O$, 5:1, pH 13.0) was added as rapidly as possible (no cooling) to 2.5 liters of rapidly stirred ice-cold acetone containing 50 g of celite. After stirring 15 minutes, the celite was filtered and washed with acetone (4×500 ml). The filtrate was examined by TLC which showed only monomeric materials.

The orange polymeric dye was extracted from the celite by eight consecutive treatments with one liter of dilute aqueous HCl (pH 3.5). This afforded 2.58 g of cationic orange dye. Elemental analysis showed that m=0.44 and n=0.56.

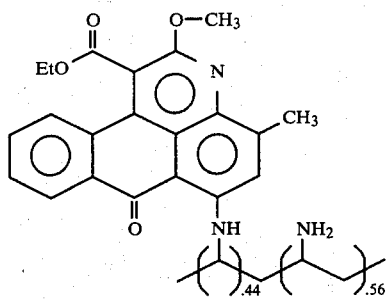

EXAMPLE XXIV

The red colorant of Example VII is employed as a dye for wool and hair. A solution of the colorant is prepared by dissolving 0.1 g of the product of Example VII in 50 ml of pH 3 water. Small samples of bleached human hair and white wool yarn are immersed in the colorant solution for 90 seconds at room temperature. Times from 10 seconds to 10 minutes may be used as well. The samples of hair and wool are removed, pressed between two filter papers, rinsed briefly in deionized water, pressed to remove rinse water, and allowed to dry at ambient conditions. The hair and the wool are colored red. A portion of each colored material is tested for color-fastness. When placed in water, there is a very slight, almost imperceptible, coloring of the test water, indicating that the polymeric colorant has formed a fast bond to the substrate.

If this experiment is repeated using other colorants prepared in the examples, similar results are achieved.

A plurality of colorants may be present in the dyeing solution. Suitable dyeing solutions are aqueous solutions which have acidic pH's, preferably from about pH 2 to about pH 5, and more preferably from pH 2.5 to pH 4.0. Also suitable are solutions having up to 80% of water-miscible organic liquids in these, preferably oxyhydrocarbon organics selected from among 1 to 4 carbon alkanols, 2 to 4 carbon alkandiols and 3 to 5 carbon alkanones, particularly methanol, ethanol, isopropanol, ethylene glycol, propylene glycol, actone, and methyl ethyl ketone. The colorant solutions may contain from about 30 ppm wt of dye to about 1.0% by weight of dye with dye contents of 100 ppm to about 0.5% being preferred and dye contents of 250 ppm to 0.2% being most preferred.

What is claimed is:

1. A process for dyeing a proteinaceous fiber substrate which comprises applying to said substrate a solution of a free amine-containing polymeric colorant comprising an aqueous solvent of pH 2.0 to 4 inclusive in which is dissolved from 100 ppm to 0.5% by weight of a polymeric colorant having the structural formula

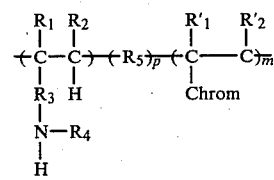

wherein $R_1$ and $R_1'$ independently are selected from hydrogen and lower saturated alkyls of 1 to 4 carbon atoms; $R_2$ and $R_2'$ independently are selected from hydrogen, lower saturated alkyls of 1 to 4 carbon atoms and phenyl; $R_3$ is selected from a simple carbon to nitrogen single covalent bond, 1 to 4 carbon atom lower saturated alkylene bridges, and a (phenylene) bridge; $R_4$ is selected from hydrogen and lower saturated alkyls of 1 to 4 carbon atoms; $R_5$ is selected from a carbon to carbon single bond, ethylene, a 1 to 4 carbon saturated alkylsubstituted ethylene, a 6-8 carbon aromatic-substituted ethylene, a

substituted ethylene wherein $R_7$ is selected from hydrogen 1 to 4 carbon alkyls, and —O—$CH_3$, an

substituted ethylene, and a nitro-substituted ethylene, Chrom is an optically chromophoric group and n, p, and m are numbers such that n is at least ½m and the sum of n+m+p is such as to assure a molecular weight of at least 2000 to the colorant molecule, and thereafter rinsing the substrate with water and drying the substrate.

* * * * *